(12) United States Patent
Elf et al.

(10) Patent No.: US 11,976,316 B2
(45) Date of Patent: May 7, 2024

(54) PHENOTYPIC CHARACTERIZATION OF CELLS

(71) Applicant: ASTREGO DIAGNOSTICS AB, Uppsala (SE)

(72) Inventors: Johan Elf, Uppsala (SE); Michael Read, Uppsala (SE); Özden Baltekin, Uppsala (SE); Martin Lovmar, Mölndal (SE); Petter Hammar, Årsta (SE); Elias Amselem, Stockholm (SE); Mikael Olsson, Uppsala (SE); Ove Öhman, Uppsala (SE)

(73) Assignee: ASTREGO DIAGNOSTICS AB, Uppsala (SE)

( * ) Notice: Subject to any disclaimer, the term of this patent is extended or adjusted under 35 U.S.C. 154(b) by 296 days.

(21) Appl. No.: 16/493,791

(22) PCT Filed: Mar. 19, 2018

(86) PCT No.: PCT/SE2018/050266
§ 371 (c)(1),
(2) Date: Sep. 13, 2019

(87) PCT Pub. No.: WO2018/174784
PCT Pub. Date: Sep. 27, 2018

(65) Prior Publication Data
US 2020/0131557 A1 Apr. 30, 2020

(30) Foreign Application Priority Data
Mar. 22, 2017 (SE) ..................... 1750341-8

(51) Int. Cl.
*G01N 33/50* (2006.01)
*C12Q 1/02* (2006.01)
*C12Q 1/04* (2006.01)
*C12Q 1/18* (2006.01)

(52) U.S. Cl.
CPC ........... *C12Q 1/18* (2013.01); *G01N 33/5008* (2013.01)

(58) Field of Classification Search
CPC .................... G01N 331/5008; C12Q 1/18
See application file for complete search history.

(56) References Cited

U.S. PATENT DOCUMENTS

| 10,041,104 B2 * | 8/2018 | Elf ........................ C12Q 1/6874 |
| 10,570,437 B2 | 2/2020 | Elf et al. |
| 2013/0196364 A1 | 8/2013 | Kwon et al. |
| 2015/0064703 A1 | 3/2015 | Super et al. |
| 2017/0023599 A1 | 1/2017 | Richards et al. |

FOREIGN PATENT DOCUMENTS

| CN | 104284984 A | 1/2015 |
| CN | 106471122 A | 3/2017 |
| WO | 03/085379 A2 | 10/2003 |
| WO | 2013/130714 A1 | 9/2013 |
| WO | 2013/130875 A1 | 9/2013 |
| WO | 2016/007068 A1 | 1/2016 |
| WO | 2016/085632 A2 | 6/2016 |

OTHER PUBLICATIONS

Baltekin, Özden et al., Fast Antibiotic Susceptibility Testing (FASTest) based on single cell growth rate measurements, bioRxiv preprint doi: http://dx.doi.org/10.1101/071407 (Aug. 26, 2016).

Dai, Jing et al., Microfluidics for Antibiotic Susceptibility and Toxicity Testing, Bioengineering, vol. 3, No. 25, pp. 1-13 (Oct. 9, 2016).

Moffat, John G. et al., Phenotypic screening in cancer drug discovery—past, present and future, Nat. Rev. Drug Discov., vol. 13, pp. 588-602 (2014).

Kim, Samuel C. et al., Miniaturized Antimicrobial Susceptibility Test by Combining Concentration Gradient Generation and Rapid Cell Culturing, Antibiotics, vol. 4, pp. 455-466 (2015).

Campbell, Jennifer et al., Microfluidic advances in phenotypic antibiotic susceptibility testing, Biomed Microdevices, vol. 18, No. 103, pp. 1-11 (Oct. 29, 2016).

* cited by examiner

*Primary Examiner* — Maryam Monshipouri
(74) *Attorney, Agent, or Firm* — Porter Wright Morris & Arthur LLP

(57) ABSTRACT

Phenotyping of cells involves loading a biological sample into a microfluidic device (1, 100) comprising cell compartments (20, 120) to capture biological material, including target cells, in the sample in the cell compartments (20, 120). A subset (20A) of the cell compartments (20, 120) is identified as comprising target cells exhibiting target phenotype characteristic(s) as determined based on monitoring biological material in the cell compartments (20, 120) prior to addition of a test agent. The biological material is exposed to a test agent and a phenotypic response of the target cells to the test agent is determined based on monitoring target cells in the identified subset (20A) of the cell compartments (20, 120). The phenotyping of the target cells is thereby not overshadowed by the response of other cells and non-cell material present in the biological sample.

15 Claims, 7 Drawing Sheets

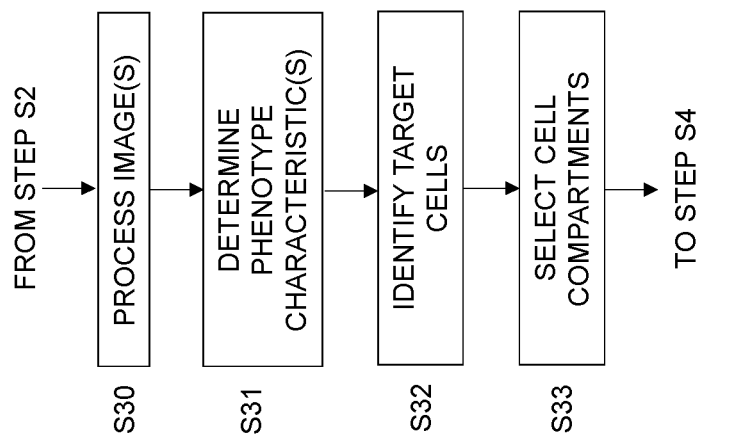
Fig. 4
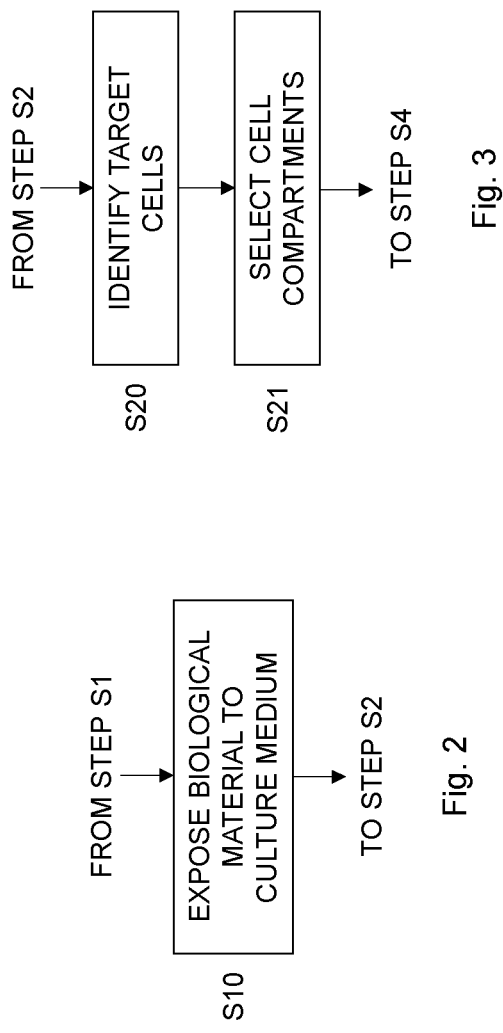
Fig. 3
Fig. 2

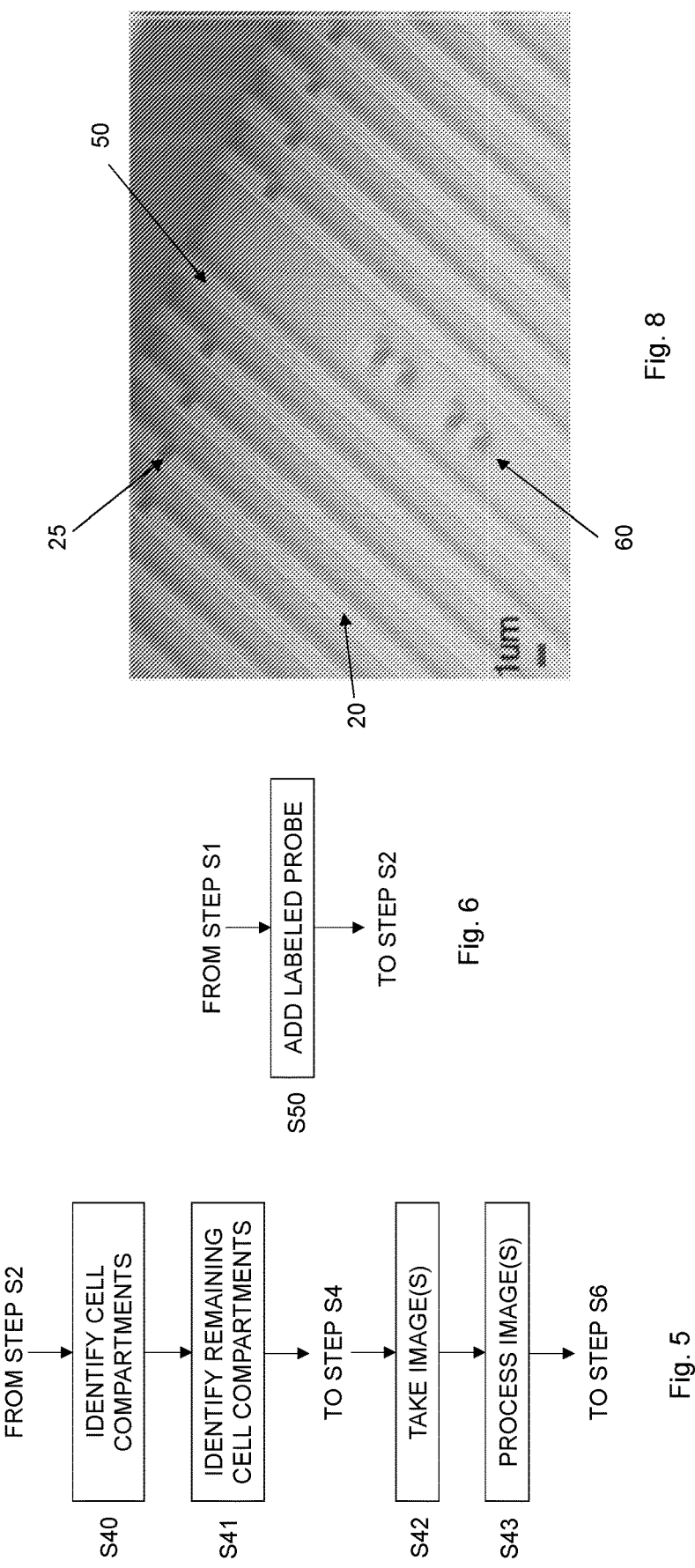

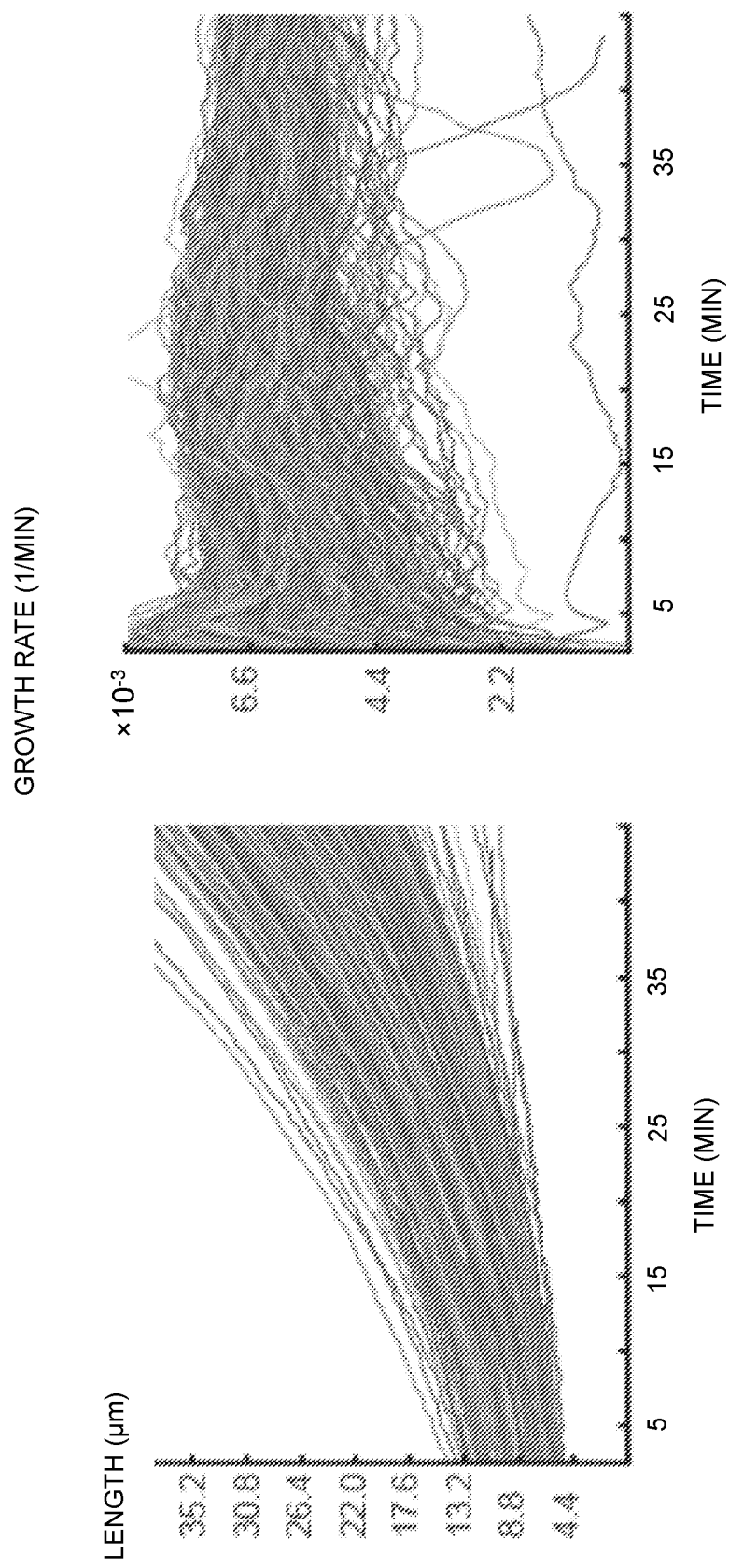

PHENOTYPIC CHARACTERIZATION OF CELLS

TECHNICAL FIELD

The present embodiments generally relate to phenotypic characterization of cells, and in particular to such phenotypic characterization of cells in a microfluidic device.

BACKGROUND

With the ever-increasing emergence and spread of antibiotic resistant bacteria, a key factor in correct treatment of infections is the ability to rapidly and robustly identify the antibiotic susceptibility profile of the infecting species in order to assure the use of an efficacious antibiotic and reduce the need for broad-spectrum drugs. Currently, a bacterial pathogen's resistance to an antibiotic is detected either by phenotyping in the absence and presence of the antibiotic, or by genotyping for the genetic markers correlated with the previously observed phenotypic resistance.

Phenotypic antibiotic susceptibility tests (ASTs) are typically based on the detection of differential bacterial growth with and without antibiotics in liquid cultures or on solid agar plates. In liquid tests, detection is based on the change in optical density, while the disk diffusion method is used on solid agar plates to identify inhibition zones. These methods are generally reliable for detecting resistance and determining the antibiotic concentration that halts bacterial growth, making them predictive of the therapeutic utility of different antibiotics. However, since it takes 1-2 days to get a reliable readout, these methods fail to provide information on how to treat a patient in the often critical, early infection stages. As a consequence, the physician is left with the difficult choice of prescribing a broad spectrum antibiotic or risking that the first prescribed antibiotic will be ineffective.

Genotypic ASTs are based on detection of specific genetic markers, such as plasmids, genes or mutations, associated with resistance phenotypes by using common genetic tools, e.g., sequence specific amplification by polymerase chain reaction (PCR), by padlock probe mediated rolling circle amplification (RCA) or whole genome sequencing. These tests are highly sensitive and can limit the detection time to what is needed to amplify selected DNA sequences to detectable levels. However, they require advance knowledge of which resistance markers to test for. If new resistance mechanisms arise, these would go undetected and result in false negatives. Furthermore, presence of certain resistance genes/mutations does not necessarily translate into phenotypic resistance.

Unlike the genotypic ASTs, the phenotypic ASTs directly assess if the antibiotic stops bacterial growth, which is the most relevant measure for the treating physician. New phenotypic ASTs have therefore been developed in recent years to decrease the detection time.

By detecting the relative abundance of 16S rRNA in liquid cultures instead of measuring optical density, the AST detection time can be pushed down to a few hours. Similarly, by reducing the growth volume and applying z-stack imaging to calculate the cell occupancy, the detection time for AST was decreased to ~100 min.

Over the last few years, microfluidics has revolutionized microbial single cell manipulation and observation, and a fruitful direction for AST is to use microfluidics to miniaturize the bacterial incubation chambers to increase the signal to background ratio. One recent example of a simple microfluidic based AST method creates a concentration gradient and applies it to small cell cultures in 30 nL chambers. Analysis of images taken every 60 min allow for detection of the minimum inhibitory concentration (MIC) in 180 min [1].

One restriction in making effective microfluidics based ASTs has been the difficulty in capturing or loading cells into the microfluidic devices. One solution is to load bacteria liquid culture mixed with liquid agarose, which solidifies upon cooling and captures the bacteria. In this approach, delivery of the antibiotic to the microfluidic agarose channel (MAC) relies on diffusion, and fast AST, typically 1-4 hours, is achieved by tracking the single cell growth rate from phase contrast images. Another solution builds on the success of MAC by moving it to a 96-well chip and combining it with single cell morphological analysis (SCMA). This method allows simultaneous identification of various responses of multiple species to various antibiotics and was able to detect methicillin resistant *Staphylococcus aureus* within 60-120 min.

A microfluidic device that can be used for phenotypic characterization of cells has been developed [2]. The microfluidic device comprises a plurality of parallel cell channels having a respective first end in fluid connection with a flow input channel and a respective second end in fluid connection with a first end of a respective wash channel. The respective second end of the wash channels is in fluid connection with a flow output channel. The cell channels have dimensions to accommodate cells in monolayer, whereas the wash channels have dimensions too small to accommodate the cells.

The microfluidic device as disclosed in [2] was used to make an AST faster than 30 min starting with only a thousand bacterial cells in less than 1 mL of liquid [3]. The fast AST is based on a microfluidic capturing technique and single cell growth rate measurements.

There is still a need for improvements within the field of cell phenotyping using microfluidic devices, and in particular when phenotyping cells present in complex and heterogeneous biological samples comprising a variety of biological and non-biological material.

SUMMARY

It is a general objective to provide a phenotyping of cells using microfluidic devices.

It is a particular objective to provide a phenotyping of cells present in heterogeneous biological samples.

These and other objectives are met by embodiments as disclosed herein.

An aspect of the embodiments relates to a method for phenotyping cells. The method comprises loading a biological sample comprising biological material including target cells into a microfluidic device comprising spatially defined and separated cell compartments to capture biological material in the spatially defined and separated cell compartments. The method also comprises monitoring biological material in the spatially defined and separated cell compartments prior to exposing biological material in the spatially defined and separated cell compartments to a test agent. The method further comprises identifying a subset of the spatially defined and separated cell compartments as comprising target cells exhibiting at least one target phenotype characteristic as determined based on the monitoring of biological material in the spatially defined and separated cell compartments. The method additionally comprises exposing biological material in the spatially defined and separated cell compartments to the test agent and monitoring target cells in the identified subset of the spatially defined and separated cell compartments. The method also comprises determining a phenotypic response of the target cells to the test agent based on the monitoring of target cells in the identified subset of the spatially defined and separated cell compartments.

The present embodiments enable efficient and accurate phenotyping of target cells present in a heterogeneous biological sample comprising various cell types and non-cell material. An initial selection is used to identify the cell compartments in the microfluidic device that are regarded as housing the target cells. The phenotyping is then made based on the response of the biological material, i.e., target cells, in the identified cell compartments while disregarding any response of material, i.e., other cells and non-cell material, in the remaining cell compartments. The phenotypic response of the target cells is thereby not overshadowed by the response of other cells and non-cell material in the heterogeneous biological sample.

BRIEF DESCRIPTION OF THE DRAWINGS

The embodiments, together with further objects and advantages thereof, may best be understood by making reference to the following description taken together with the accompanying drawings, in which:

FIG. 2 is a flow chart illustrating an additional, optional step of the method shown in FIG. 1;

FIG. 3 is a flow chart illustrating an embodiment of the identifying step S3 in FIG. 1;

FIG. 4 is a flow chart illustrating another embodiment of the identifying step S3 in FIG. 1;

FIG. 5 is a flow chart illustrating a further embodiment of the identifying step S3 and an embodiment of the monitoring step S5 in FIG. 1;

FIG. 6 is a flow chart illustrating an additional, optional step of the method shown in FIG. 1;

FIG. 8 is a scanning electron microscopy image showing part of the mold for a microfluidic device according to an embodiment (magnification: $11 \times 10^3 \times$);

FIGS. 11A and 11B show length (FIG. 11A) and growth rate (FIG. 11B) as a function of time plotted for individual cell channels of a microfluidic device;

DETAILED DESCRIPTION

Figure 1:
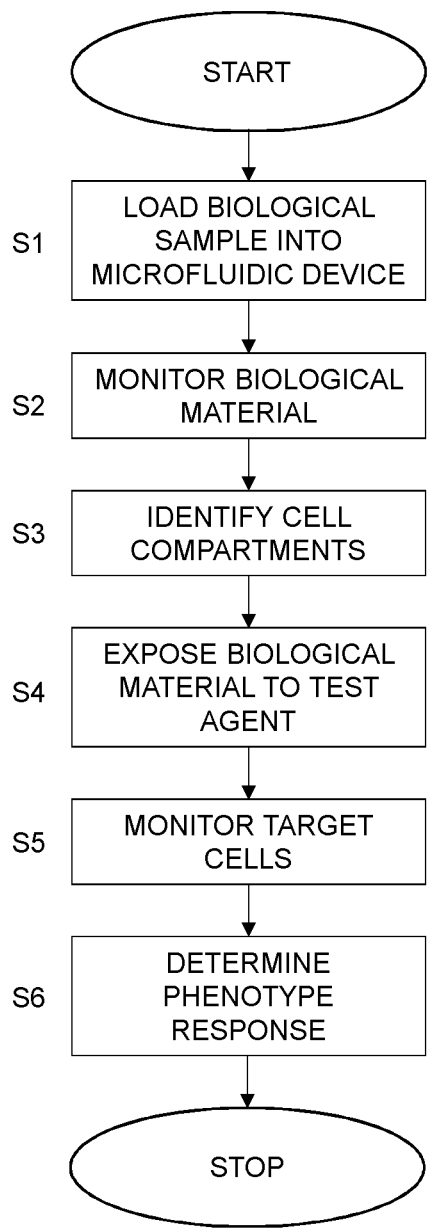
FIG. 1 is a flow chart illustrating a method for phenotyping according to an embodiment.

The present embodiments generally relate to phenotypic characterization of cells, and in particular to such phenotypic characterization of cells in a microfluidic device.

Microfluidic devices, also denoted microfluidic chips in the art, can be used for phenotyping, i.e., phenotypic characterization, of cells in a time efficient way. However, in real-life applications the biological sample input to the microfluidic devices can be a complex and heterogeneous sample comprising various biological material including target cells to be phenotyped, other cells and cellular debris, and non-biological material, such as dirt, contaminants, etc. Hence, the biological sample is most often heterogeneous and the target cells may in fact constitute a minority, even a minute minority, of the material present in the biological sample.

The heterogeneity of the biological sample may be due to various reasons. For instance, the biological sample may in itself consist of various cell types and non-cell material as taken from an animal or human subject. Alternatively, or in addition, the biological sample may be contaminated during the sampling and/or up to the point of loading the biological sample into the microfluidic device. A typical example of the latter is a urine midstream sample. It is not uncommon for such a urine midstream sample to include cellular and microbial contamination, such as cells and bacteria from the skin of the patient.

Thus, there may be problems and difficulties in phenotyping target cells in a biological sample in a microfluidic device due to the heterogeneity of the biological sample and the presence of other cells and non-cell material that may negatively affect the phenotypic characterization.

For instance, phenotyping target cells may be performed by monitoring the response of target cells to a stimuli, such as exposure to a test agent, a particular environmental condition, etc. If the target cells constitute a minority of the material that is captured and monitored in the microfluidic device the phenotyping may be flawed by the presence of other cells and non-cell material. In the worst case, the phenotypic characterization of the target cells may be incorrect thereby assigning an incorrect phenotype to the target cells.

A typical example is testing antibiotic susceptibility of bacteria present in urine from a patient suffering from urinary tract infection (UTI). If the urine sample is contaminated by cells and bacteria from, for instance, the skin, such contaminating cells may constitute the vast majority of the cells in the urine sample loaded into the microfluidic device. The contaminating bacteria may, however, not grow or survive in the urine sample due to the constituents and pH of the urine sample. If the cells loaded in the microfluidic device are exposed to an antibiotic to test the susceptibility of the UTI-causing bacteria in the urine then most of the captured cells will not grow, not mainly because the presence of the antibiotic but due to the contaminating cells will not grow in urine. Monitoring the growth of cells in the microfluidic device in the presence of antibiotic may therefore conclude that UTI-causing bacteria are susceptible to the antibiotic since most of the cells captured in the microfluidic device do not grow in the presence of antibiotic. This means that the growth of resistant bacteria in the urine may be overshadowed by the non-growth of the cells that are not viable in urine. As a result, the UTI-causing bacteria in the urine may be incorrectly classified as susceptible to the antibiotic even if they really are resistant to the antibiotic. This may in turn have grave consequences when treating a patient, from whom the urine sample was taken, by administering an antibiotic that will not significantly inhibit growth of the resistant bacteria present in the patient's urine.

The present embodiments provide a method for phenotyping cells that solves the above mentioned problem of loading a complex or heterogeneous biological sample into a microfluidic device with the purpose of phenotyping so-called target cells present in the biological sample.

In the following, "target cells" denote cells, such as bacteria, e.g., *Escherichia, Klebsiella, Staphylococcus* cells, archaea cells, eukaryotic cells, yeast cells, animal cells, human cells, cancer cells, etc., present in a biological sample. These target cells should be phenotyped, i.e., at least one phenotypic characteristic of the target cells is determined in the method of the embodiments.

The microfluidic device used in the method for phenotyping cells comprises spatially defined and separated cell compartments, or cell compartments for short. Such cell compartments are designed to capture and house biological material present in the biological sample. Accordingly, when loading the biological sample into the microfluidic device biological material, such as cells, present in the biological sample is captured by the cell compartments. The cell compartments are spatially defined and separated. This means that each cell compartment has a spatially defined position in the microfluidic device and each cell compartment is separated, typically physically separated, from other cell compartments in the microfluidic device. Accordingly, it is possible to physically separate and individually monitor biological material in the spatially defined and separated cell compartments of the microfluidic device.

A cell compartment can be any physical structure or part of the microfluidic device that is dimensioned and designed to capture and house cells. Non-limiting but illustrative examples of such cell compartments include cell channels, cell traps, etc.

FIG. 1 is a flow chart illustrating a method for phenotyping cells according to an embodiment. The method comprises loading, in step S1, a biological sample comprising biological material including target cells into a microfluidic device. The microfluidic device comprises spatially defined and separated cell compartments to capture biological material in the spatially defined and separated cell compartments. A next step S2 comprises monitoring biological material in the spatially defined and separated cell compartments prior to exposing biological material in the spatially defined and separated cell compartments to a test agent. A subset of the spatially defined and separated cell comportments is identified in step S3 as comprising target cells exhibiting at least one phenotypic characteristic as determined based on the monitoring of biological material in the spatially defined and separated cell compartments in step S2.

Biological material in the spatially defined and separated cell compartments is exposed to the test agent in step S4. A following step S5 comprises monitoring target cells in the identified subset of the spatially defined and separated cell compartments. A phenotypic response of the target cells to the test agent is then determined in step S6 based on the monitoring of target cells in the identified subset of the spatially defined and separated cell compartments in step S5.

The method of the embodiments thereby involves a selection step to identify those spatially defined and separated cell compartments of the microfluidic device that comprise target cells prior to determining the phenotypic response of the target cells. Thus, biological material captured or loaded in the spatially defined and separated cell compartments is monitored to identify the spatially defined and separated cell compartments that comprise biological material exhibiting the at least one target phenotype characteristic. The phenotypic response is then determined in step S6 based only on the response of the biological material, i.e., target cells, that is present in the spatially defined and separated cell compartments identified in step S3. Accordingly, biological material in the remaining spatially defined and separated cell compartments induce cells and non-cell material other than the target cells as determined based on not exhibiting the at least one target phenotype. The responses of such material in the remaining spatially defined and separated cell compartments are thereby disregarded and not used when determining the phenotypic response in step S6.

This mean that the phenotypic response as determined in step S6 is in fact the true response of the target cells to the test agent in the biological material and this phenotypic response will not be overshadowed or affected by the responses of other cells and non-cell material in the biological sample.

For instance, assume that the biological sample is a urine sample taken from a patient suffering from UTI and that the susceptibility of UTI-causing bacteria as target cells to an antibiotic is to be tested in the method shown in FIG. 1. The urine sample is then loaded in step S1 into the microfluidic device to capture the UTI-causing bacteria and any contaminating bacteria and cells in the spatially defined and separated cell compartments. The contaminating bacteria and cells may not be viable in the urine and will thereby not grow or at least grow slowly. Accordingly, step S2 may, for instance, involve monitoring the biological material in the spatially defined and separated cell compartments with the purpose of determining their viability or cell growth, such as by studying the length extension of the cells over a period of time. Step S3 may therefore involve identifying the subset or portion of the spatially defined and separated cell compartments that comprises cells that are viable and/or have a growth rate exceeding a target growth rate as determined based on the monitoring in step S2. The biological material in this identified subset is thereby viable and grows well in the urine and thereby mainly constitutes of the UTI-causing bacteria. Material in the remaining spatially defined and separated cell compartments is not viable and has a growth rate below the target growth rate. This material thereby mainly consists of contaminating cells and bacteria and non-cell material from the urine sample.

The biological material in the spatially defined and separated cell compartments is then exposed to the antibiotic and the biological material, i.e., UTI-causing bacteria, present in the spatially defined and separated cell compartments identified in step S3 is monitored in step S5 and the phenotypic response of this biological material, i.e., UTI-causing bacteria, to the antibiotic is then determined in step S6 based on the monitoring in step S5. The susceptibility or resistance of the UTI-causing bacteria to the antibiotic can thereby efficiently be determined in step S6 without the risk of overshadowing or influence from the response of the contaminating cells or bacteria from the urine sample.

Hence, according to the present embodiments an initial monitoring of biological material in the spatially defined and separated cell compartments is first performed in step S2 before exposing the biological material in the spatially defined and separated cell compartments to the test agent in step S4. The initial monitoring in step S2 is performed prior to addition of the test agent in order to identify at least one subset of the spatially defined and separated cell compartments to monitor once the test agent has been added. If the test agent would be present already in step S2, it would be hard or even impossible to differentiate between dead or non-viable cells and non-cell material from cells that are susceptible to the test agent and thereby not able to grow in the presence of the test agent. Thus, the monitoring in step S2 and the subsequent identification in step S3 are performed in order to identify those spatially defined and separated cell compartments that comprise viable cells, capable of growing in the spatially defined and separated cell compartments, and differentiate such spatially defined and separated cell compartments from those that contain non-viable cells and non-cell material.

In an embodiment, the initial monitoring in step S2 is performed for at least a minimum period of time in order to enable a correct identification of the spatially defined and separated cell compartments that comprises target cells in step S3. For instance, the monitoring in step S2 is performed at least 1 minute, at least 2 minutes, at least 3 minutes, at least 4 minutes, at least 5 minutes, at least 6 minutes, at least 7 minutes, at least 8 minutes, at least 9 minutes or at least 10 minutes. The actual minimum period of time is typically dependent on the target cells and the particular phenotypic characteristic. For instance, if the phenotypic characteristic is growth of the target cells, the minimum period of time is preferably set to allow the target cells to divide at least once. Hence, the minimum period of time could be set based on the average cell cycle or cell division time of the target cells.

In an embodiment, the biological sample is a body fluid sample, such as a urine sample, a blood sample, a saliva sample, a feces sample, a cerebrospinal fluid sample, an amniotic fluid sample, a milk sample, or a lymph sample. Alternatively, the biological sample could be obtained from a body tissue, such as a biopsy. Other examples include food sample tested for bacterial contaminations, milk from cow, goats or other milk producing animals for mastitis testing, etc. Actually, any biological sample that comprises cells and that can be loaded into a microfluidic device can be used according to the embodiments.

In the following disclosure, step S4 is described and exemplified by exposing the biological material in the spatially defined and separated cell compartments to a test agent. This test agent could be any molecule, compound, composition, or a mixture of molecules, compounds or compositions. In related embodiments, the biological material is more generally exposed to a stimuli in the spatially defined and separated cell compartments. Such a stimuli does not necessarily have to be a test agent but could instead be a change in environmental conditions, such as temperature change. Thus, the phenotypic response of the target cells to the stimuli is then determined in step S6.

FIG. 2 is a flow chart illustrating an additional, optional step of the method shown in FIG. 1. The method continues from step S1 in FIG. 1. A next step S10 comprises exposing biological material in the spatially defined and separated cell compartments to a culture medium. The method then continues to step S2 in FIG. 1, which comprises, in this embodiment, monitoring biological material exposed to the culture medium in the spatially defined and separated cell compartments.

In an embodiment, the biological sample itself is regarded as the culture medium. Thus, any biological material in the biological sample and captured in the spatially defined and separated cell compartments is exposed to the biological material as the culture medium. In this embodiment, there is no need for any medium exchange.

In an alternative embodiment, there is a medium change following loading the biological sample in step S1. Thus, biological material from the biological sample as captured in the spatially defined and separated cell compartments is then exposed to a new culture medium in step S10. This culture medium is then preferably selected so that the target cells will exhibit the at least one target phenotypic characteristic when exposed to the culture medium whereas other cells and non-cell material will preferably not exhibit the at least one target phenotypic characteristic when exposed to the culture medium in step S10.

This switch of culture media could be performed more than once in order to expose biological material in the spatially defined and separated cell compartments to different culture media. The culture medium or media could be a general culture medium containing all the elements that most cells need for growth and are not selective. Alternative, the culture medium or media could be a minimal culture medium containing the minimum nutrients possible for cell growth, generally without the presence of amino acids. Such minimal culture media may be used to grow "wild-type" cells and select for or against recombinants or exconjugants. A further alternative is to use a culture medium or media that is selective, i.e., supports growth of only selected cells. A related variant is to use a differential culture medium or media to distinguish one cell type from another growing on the same culture medium. This type of culture media uses the biochemical characteristics of a cell growing in the presence of specific nutrients or indicators added to the culture medium to visibly indicate the defining characteristics of the cell.

In the case of switching between different culture media, all of the culture media can be of a same type (general culture medium, minimum culture medium, selective culture medium or differential culture medium) or the switch could be between different culture media types.

For instance, different selective culture media having different carbon sources could be used in connection with UTI-causing bacteria in order to identify different populations of target cells, which is further described herein. For instance, UTI-causing *Escherichia coli* can grow in a culture medium comprising arabinose, lactose, mannitol or xylose as a carbon source but not in citrate. *Klebsiella pneumoniae* can be culture using any of the above mentioned carbon sources, whereas *Proteus mirabilis* will only grow using citrate or xylose as carbon source and not arabinose, lactose or mannitol. Correspondingly, *Staphylococcus epidermidis* only use lactose as carbon source and not arabinose, citrate, mannitol or xylose.

In an embodiment, step S4 of FIG. 1 comprises exposing the biological material in the spatially defined and separated cell compartments to the culture medium comprising the test agent or to another culture medium comprising the test agent.

In the first embodiment, the test agent is added to the same culture medium that was used in step S10 of FIG. 2, such as added to the biological sample if the biological sample is used as culture medium. In this embodiment, there is no need for any culture exchange between step S10 and step S4. Thus, the only difference is the addition of the test agent into the culture medium in step S4.

In the latter embodiment, there is a culture medium exchange in step S4. Thus, a different culture medium comprising the test agent is used in step S4 as compared to the culture medium used in step S10. This different culture medium could then be selected and adapted to the inclusion of the test agent and monitoring the response of the target cells to the test agent in the different culture medium.

Step S3 in FIG. 1 comprises identifying the subset of the spatially defined and separated cell compartments as comprising target cells exhibiting at least one target phenotype characteristic as determined based on the monitoring in step S2. In an embodiment, biological material exhibiting one target phenotype characteristic is determined in step S3 to be target cells and the spatially defined and separated cell compartments comprising such biological material are included in the identified subset in step S3. Material not exhibiting this target phenotype characteristic is thereby not regarded as target cells and the spatially defined and separated cell compartments comprising such material should not be included in the identified subset in step S3.

In another embodiment, biological material exhibiting multiple, i.e., at least two, target phenotype characteristics is determined in step S3 to be target cells and the spatially defined and separated cell compartments comprising such biological material are included in the identified subset in step S3. Material not exhibiting any of the multiple target phenotype characteristics or merely exhibiting some but not all of the multiple target phenotype characteristics is not regarded as target cells and the spatially defined and separated cell compartments comprising such material should not be included in the identified subset in step S3.

Illustrative, but non-limiting, examples of target phenotype characteristics could be growth rate, shape, size, form of growth rate curve defining growth rate over time, form of length curve defining cell length over time, form of area curve defining cell area over time, color, optical density, electrical conductivity, heat production, surface antigen composition as observed by affinity reagents, absorption spectra, and a mixture of at least two such phenotype characteristics.

A target phenotype characteristic can be the complement of a characteristic of the non-target cell material. Thus, target phenotype characteristic could be the lack of a given phenotypic characteristic. In such a case, non-target cell material exhibit the phenotypic characteristic, whereas the target cells have the target phenotype characteristic by not exhibiting the given phenotypic characteristic.

Growth rate in a given culturing condition, such as culture medium, is a phenotypic characteristic or trait that can advantageously be used to discriminate target cells from other material. Growth rate can be determined, for instance, by monitoring the number of cells or particles in each spatially defined and separated cell compartment as the number will increase over time for growing cells. Alternatively, or in addition, grow rate can be determined by monitoring the length of the portion of a spatially defined and separated cell compartment occupied by cells or particles. This length will increase over time for growing cells but remain the same for non-viable and non-growing cells and non-cell material. FIG. 11A illustrates such length over time in spatially defined and separated cell compartments of a microfluidic device. Alternatively, or in addition, grow rate can be determined by monitoring the area or length of cells segmented in images of the spatially defined and separated cell compartments.

The growth rate over time typically varies between different cell types. For instance, some cell types grows exponentially, whereas other grow in more periodic ways. Accordingly, the shape or form of the growth rate curve can be used to discriminate target cells from other cells and non-cell material. FIG. 11B illustrates growth rate curves of material captured in spatially defined and separated cell compartments of a microfluidic device.

Other phenotypic characteristics that vary between different cell types and between cells and non-cell material include the shape, size, color and optical density. Thus, various cell types may have different shapes, such as rod-shaped, spherical, twisted, disc-shaped, etc. Also the size, such as length and/or diameter, is a phenotypic characteristic that can be used to differentiate cells from each other and from non-cell material, such as ranging from sub-µm up to several tens of µm.

Optical density, color or other spectral properties differ between different cell types, such as depending on contents of the cells, shape of the cells, etc., and between cells and non-cell material. Thus, optical properties of the material in the spatially defined and separated cell compartments can be used to differentiate cells, non-target cells and non-cell material.

Conductivity and heat production will depend on the chemical composition and metabolic state of the cells and can therefore constitute the basis for differentiating target cells from non-target cells.

FIG. 3 is a flow chart illustrating an embodiment of step S3 in FIG. 1. In this embodiment step S3 comprises identifying, in step S20, target cells exhibiting the at least one target phenotype as determined based on the monitoring of biological material in the spatially defined and separated cell compartments in step S2. A next step S21 then comprises selecting the subset of the spatially defined and separated cell compartments as a subset of the spatially defined and separated cell compartments comprising the identified target cells.

Hence, in this embodiment biological material in the spatially defined and separated cell compartments is monitored in step S2. The following step S20 identifies the biological material, i.e., target cells, exhibiting the at least one target phenotype characteristic as determined based on the monitoring in step S2. The spatially defined and separated cell compartments comprising the biological material identified in step S20 are then selected in step S21 as the subset of the spatially defined and separated cell compartments comprising target cells.

In an embodiment, step S2 comprises monitoring, at multiple time instance, biological material in the spatially defined and separated cell compartments.

This embodiment is in particular suitable for usage in connection with target phenotype characteristics in the form of growth rate and/or form of growth rate curve. Hence, in order to determine or at least estimate the growth rate or determine the form of growth rate curve the biological material in the spatially defined and separated cell compartments need to be monitored at multiple time instances in step S2.

However, for other target phenotype characteristics, such as shape, size, color and optical density it may be sufficient to monitor the biological material in the spatially defined and separated cell compartments only once in step S2.

Correspondingly, step S5 comprises, in an embodiment, monitoring, at multiple time instances, target cells in the identified subset of the spatially defined and separated cell compartments. Thus, depending on the particular phenotypic response of the target cells to the test agent it might be sufficient to monitor the target cells once in step S5 or at multiple time instances.

In an embodiment, step S2 comprises taking at least one image of the spatially defined and separated cell compartments. Correspondingly, in an embodiment, step S5 comprises taking at least one image of the target cells in the identified subset of the spatially defined and separated cell compartments. A single image at a single time instance could be taken in these embodiments of steps S2 and S5. Alternatively, multiple images at multiple time instances are taken in step S2 and/or S5.

In a particular embodiment, the at least one image taken in step S2 and/or S5 is taken using a microscopy, such as a phase contrast microscope, connected to a camera, such as charge-coupled device (CCD) and complementary metal-oxide semiconductor (CMOS) camera, or a confocal scanning system for fluorescence, Raman imaging, Coherent Anti-stokes Raman Scattering (CARS), Stimulated Raman Scattering (SRS) and similar chemically sensitive techniques that gives spectral changes for dead and live cells. This includes measurements in one or several wavelengths with or without contrast enhancing additions to the growth media, such as chemically specific probes and dyes.

Conductivity and/or heat production could be measured by electrodes or sensors arranged in or in connection with the spatially defined and separated cell compartments.

FIG. 4 is a flow chart illustrating an embodiment of step S3 in FIG. 1 when step S2 comprises taking at least one image of the spatially defined and separated cell compartments. In this embodiment, step S3 comprises processing, in step S30, the at least one image for detection of the spatially defined and separated cell compartments and biological material in the spatially defined and separated cell compartments. At least one respective phenotype characteristic of biological material in the spatially defined and separated cell compartments is determined in step S31 based on the processing. A following step S32 comprises identifying target cells as biological material in the spatially defined and separated cell compartments and having at least one respective determined phenotype characteristic corresponding to the at least one target phenotype characteristic. Step S33 comprises selecting the subset of the spatially defined and separated cell compartments as a subset of the spatially defined and separated cell compartments comprising the identified target cells.

In this embodiment, the at least one image taken as previously described herein is processed to identify the spatially defined and separated cell compartments and the biological material present therein in step S30. At least one respective phenotype characteristic is determined for the biological material in the spatially defined and separated cell compartments in step S31 based on the processing of step S30. For instance, assume that the target phenotype characteristic is a growth rate exceeding a threshold rate $T_R$. Further assume that the microfluidic device comprises N spatially defined and separated cell compartments. In such a case, a respective growth rate $R_i$, i=1 . . . N is determined for the respective material in each of the N spatially defined and separated cell compartments in step S31. Target cells are then identified as biological material having a respective growth rate $R_i$ exceeding the threshold rate, i.e., $R_i > T_R$. This means that the biological material in the N spatially defined and separated cell compartments can be classified or identified as either target cells if $R_i > T_R$ and other cells or non-cell material if $R_i \leq T_R$. The spatially defined and separated cell compartments among the N spatially defined and separated cell compartments comprising biological material identified in step S32 as target cells, i.e., having $R_i > T_R$, are then selected in step S33. The other spatially defined and separated cell compartments are remaining spatially defined and separated cell compartments comprising other material than the target cells. In such a case, the phenotypic response is subsequently determined in step S6 based only on the phenotypic response of the biological material in the spatially defined and separated cell compartments selected in step S33 and thereby identified as comprising the target cells.

FIG. 5 is a flow chart illustrating embodiments of steps S3 and S5 in FIG. 1. In this case, step S1 of FIG. 1 comprises loading a biological sample comprising biological material including the target cells and non-target cells into the microfluidic device to capture biological material in the spatially defined and separated cell compartments. The method then continues to step S2 in FIG. 1 and then further to step S40 in FIG. 5. Step S40 comprises identifying a subset of the spatially defined and separated cell compartments as comprising target cells exhibiting the at least one target phenotype characteristic as determined based on the monitoring of biological material in the spatially defined and separated cell compartments in step S2. Step S41 correspondingly comprises identifying remaining spatially defined and separated cell compartments as comprising non-target cells and/or non-cell material not exhibiting the at least one target phenotype characteristic as determined based on the monitoring of biological material in the spatially defined and separated cell compartments in step S2.

The method then continues to step S4 in FIG. 1 and then further to step S42 in FIG. 5. Step S42 comprises taking at least one image of the spatially defined and separated cell compartments. The at least one image is processed in step S43 for detection of the identified subset of the spatially defined and separated cell compartments and target cells in the identified subset of the spatially defined and separated cell compartments while disregarding the remaining spatially defined and separated cell compartments and the non-target cells and/or non-cell material in the remaining spatially defined and separated cell compartments.

In an embodiment, the method then continues to step S6, where the phenotypic response of the target cells to the test agent is determined based on the processing in step S43, i.e., based on the phenotypic response of the target cells, i.e., biological material in the subset of spatially defined and separated cell compartments identified in step S40, but not based on any response of the non-target cells and/or non-cell material, i.e., material in the remaining portion of the spatially defined and separated cell compartments identified in step S41.

Thus, the phenotypic response as determined in step S6 is thereby determined based only on the response of the biological material identified or selected as being target cells and present in the spatially defined and separated cell compartments identified in step S40 and thereby not on the response of biological material and/or non-biological material present in the remaining spatially defined and separated cell compartments identified in step S41. This approach thereby effectively prevents any response of non-target cells and non-cell material from overshadowing the phenotypic response of the target cells to the test agent.

In an embodiment, the monitoring conducted in step S5 could thereby involve monitoring all spatially defined and separated cell compartments, i.e., the subset of the spatially defined and separated cell compartments comprising target cells and the remaining spatially defined and separated cell compartments. However, the phenotypic response determined in step S6 is preferably only determined based on the biological material, i.e., target cells, present in the subset of the spatially defined and separated cell compartments identified in step S3.

In the foregoing, the embodiments have mainly been described in connection with identifying and separating so-called target cells from other biological and non-biological material in the spatially defined and separated cell compartments. It is, however, also possible, within a same microfluidic device, to identify different target cell populations exhibiting different target phenotype characteristics or different combinations of target phenotype characteristics.

For instance, step S3 could comprise identifying a first subset of the spatially defined and separated cell compartments as comprising a first population of target cells exhibiting first target phenotype characteristic(s) and identifying a second subset of the spatially defined and separated cell compartments as comprising a second population of target cells exhibiting second target phenotype characteristic(s) as determined based on the monitoring of biological material in the spatially defined and separated cell compartments in step S2.

In this embodiment, step S5 comprises monitoring the first population of target cells in the identified first subset of the spatially defined and separated cell compartments and monitoring the second population of target cells in the identified second subset of the spatially defined and separated cell compartments.

Step S6 preferably comprises, in this embodiment, determining a respective phenotypic response of the first population of target cells and the second population of target cells to the test agent based on the monitoring of the first population of target cells in the identified first subset of the spatially defined and separated cell compartments and of the second population of target cells in the identified second subset of the spatially defined and separated cell compartments in step S5.

The above described embodiment can of course also be applied to cases with three or more populations of target cells.

In an embodiment, fluorescent probes specifically binding to a marker is added prior to or in connection with the monitoring in step S2. In such a case, step S2 comprises monitoring biological material in the spatially defined and separated cell compartments by measuring fluorescence in the spatially defined and separated cell compartments. In this embodiment, the target phenotype characteristic could then be the presence of the marker, thereby resulting in presence of fluorescent probes and high measured fluorescence, or the absence of the marker, thereby resulting in the absence of fluorescent probes and comparatively low measured fluorescence.

Thus, step S3 preferably comprises identifying the subset of the spatially defined and separated cell compartments as comprising target cells exhibiting the at least one target phenotype characteristic as determined based on the measured fluorescence in the spatially defined and separated cell compartments.

The fluorescent probe binds specifically to a marker. This marker can be a molecule, the presence of which is to be used in the selection or identification in step S3. For instance, the marker could be a protein in the cells or in the cell membrane, such as a receptor. Alternatively, the marker could be a nucleic acid molecule, such as a particular DNA or gene sequence or a particular mRNA sequence.

The fluorescent probe can, for instance, be an intercalating DNA binding dye that clearly distinguishes cells with chromosomes from cell debris. The fluorescent probe can be a life-death screening dye, that only enters live cells.

The fluorescent probe can be a fluorescent antibody that binds specifically to selected cells, which enables differentiation of for example, different bacterial species with different surface antigens, cancer cells from other cells based on surface antigens, circulating fetal cells from the pregnant woman's own cells.

The fluorescent probe can be a fluorescent oligonucleotide that targets a species specific RNA, such as the 16S ribosomal RNA.

Specifically binding of a fluorescent probe can be determined based on affinity and/or avidity. The affinity, represented by the equilibrium constant for the dissociation of the target marker with the fluorescent probe ($K_d$), is a measure for the binding strength between the target maker and the fluorescent probe. The lesser the value of $K_d$, the stronger the binding strength. Alternatively, the affinity can also be expressed as the affinity constant ($K_a$), which is $1/K_d$. As will be clear to the skilled person, affinity can be determined in a manner known per se, depending on the specific target marker of interest.

Avidity is the measure of the strength of binding between a fluorescent probe and the target marker. Avidity is related to both the affinity between the target marker and the binding site on the fluorescent probe and the number of binding sites present on the fluorescent probe.

Generally, any $K_d$ value greater than $10^{-4}$ M (or any $K_a$ value lower than $10^4 \, M^{-1}$) is generally considered to indicate non-specific binding.

Specific binding of a fluorescent probe to a target maker can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art.

In the foregoing, the probe has been exemplified by a fluorescent probe. The embodiments are, however, not limited thereto. Actually any probe that can be detectable and measured could be used according to the embodiments, such as fluorescent probes, dyed probes, chemiluminescent probes, radiolabeled probes, etc.

Hence, in an embodiment, the method comprises an additional step as illustrated in FIG. 6. The method continues from step S1 in FIG. 1. A next step S50 comprises adding a labeled probe to the spatially defined and separated cell compartments. The method then continues to step S2 in FIG. 1, which comprises, in this embodiment, monitoring the labeled probe in the spatially defined and separated cell compartments. In this embodiment, step S3 preferably comprises identifying the subset of the spatially defined and separated cell compartments as comprising target cells exhibiting at least one target phenotype characteristic as determined based on the monitoring of the labeled probe in the spatially defined and separated cell compartments in step S2.

It is also possible to use probes with different detectable labels or properties, such as with different spectral properties, in parallel to distinguish several target cell populations at the same time.

In a first implementation example the test agent is an antibiotic. In this implementation example, the method is used for determining a susceptibility of target cells to the antibiotic. Hence, step S6 of FIG. 1 comprises determining a susceptibility of the target cells to the antibiotic based on the monitoring of target cells in the identified subset of the spatially defined and separated cell compartments in step S5.

In this implementation example, the method can be used in a fast AST typically presenting results indicating whether the target cells, i.e., target bacteria, are susceptible or not to the antibiotic within less than 30 minutes. This should be compared to the golden standard today of phenotypic ASTs requiring 1-2 days to get reliable results.

A typical application of such an implementation example would be to conduct an AST of bacteria present in a body fluid sample, such as urine, blood, saliva, feces, cerebrospinal fluid, milk, amniotic fluid or lymph.

In a second implementation example, the test agent is a cytostatic. In such an implementation example, step S6 of FIG. 1 comprises determining a susceptibility of the target cells to the cytostatic based on the monitoring of target cells in the identified portion of the spatially defined and separated cell compartments in step S5.

The target cells to be phenotyped in this implementation examples are preferably cancer cells, the susceptibility to a cytostatic is to be tested.

Figure 7:
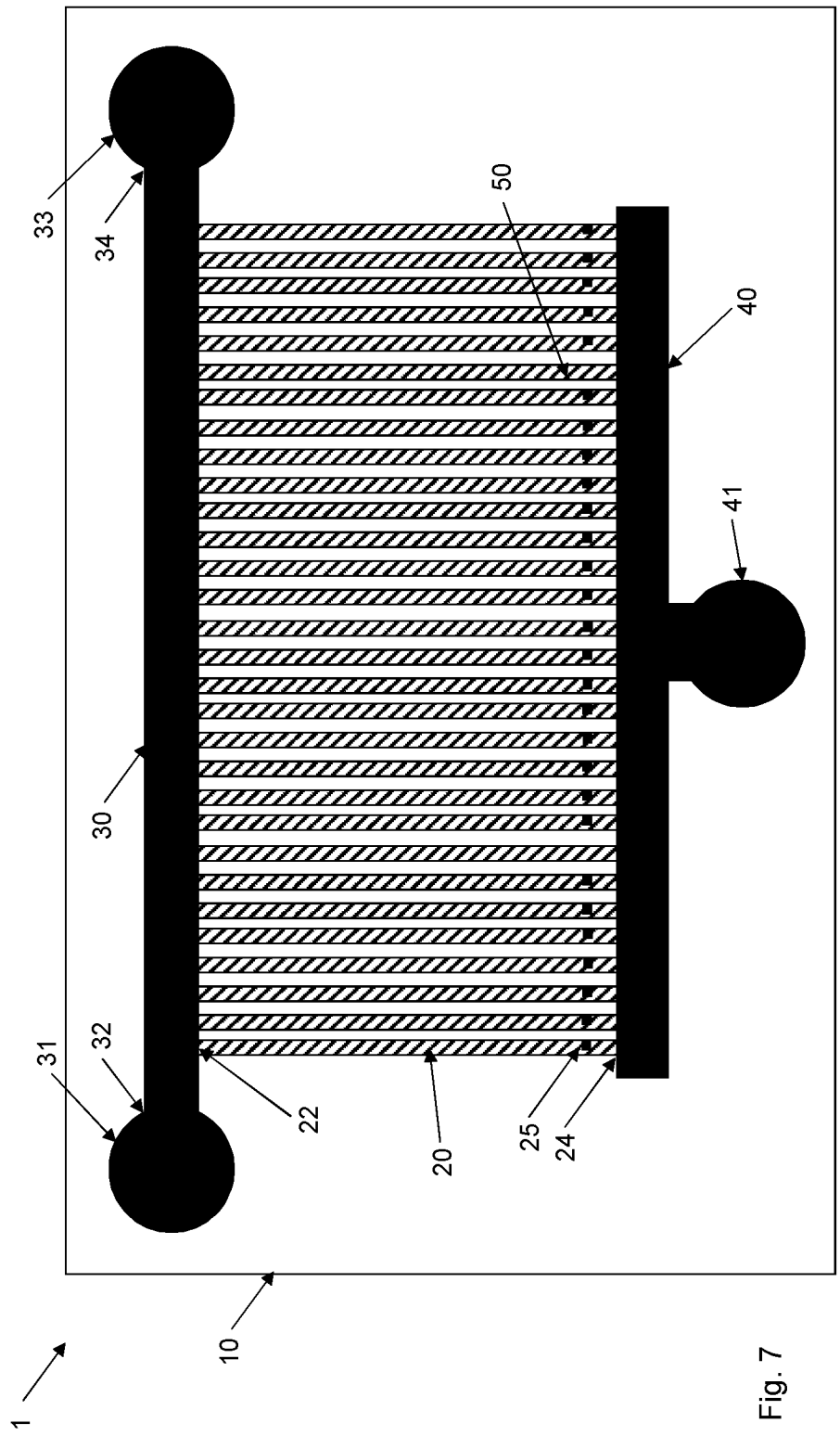
FIG. 7 is an illustration of a microfluidic device that can be used in the method for phenotyping according to an embodiment.

FIG. 7 is a schematic illustration of a microfluidic device 1 that can be used in the method of the embodiments. This microfluidic device 1 is further described in [2, 3, 5]. Briefly, the microfluidic device 1 comprises a substrate 10 having spatially defined and separated cell channels 20, also denoted cell traps, having a dimension to accommodate cells. A respective first end 22 of the spatially defined and separated cell channels 20 is in fluid connection with a flow input channel 30 having a first end 32 in fluid connection with a first fluid port 31 and a second end 34 in fluid connection with a second fluid port 33. A respective second end 24 of the spatially defined and separated cell channels 20 is in fluid connection with a flow output channel 40 in fluid connection with a third fluid port 41. The spatially defined and separated cell channels 20 comprise a respective channel obstruction 25 designed to prevent selected cells, such as of a particular size, dimension, shape or form, from passing the respective channel obstruction 25 and into the flow output channel 40.

If the microfluidic device 1 as defined above and illustrated in FIG. 7 is used in the method then step S1 of FIG. 1 preferably comprises, in an embodiment, loading the biological sample into the first fluid port 31 allowing excessive biological sample to flow out through the third fluid port 41 and optionally the second fluid port 33 to capture biological material in the spatially defined and separated cell channels 20 by the channel obstructions 25.

Thus, the biological sample is input into the first fluid port 31 and is allowed to flow through the flow input channel 30 preferably towards and optionally out from the second fluid port 33. In addition, the biological sample including the target cells will flow into the spatially defined and separated cell channels 20 and further into the flow output channel 40 and the third fluid port 41.

The spatially defined and separated cell channels 20 are dimensioned, i.e., having size, such as width and height, and shape, to allow selected cells to enter the spatially defined and separated cell channels 20. Cells or non-cell material having a size and/or shape that is too big or not adapted to the cross-sectional size and shape of the spatially defined and separated cell channels 20 will not enter the spatially defined and separated cell channels 20 but rather flow out from the flow input channel 30 through the second fluid port 33.

The channel obstruction 25 of the spatially defined and separated cell channels 20 is designed to have a shape and dimension, such as width and/or height, that prevent the selected cells from passing the channel obstruction 25 and enter the flow output channel 40. Accordingly, the selected cells will become trapped and captured in the spatially defined and separated cell channels 20.

In an embodiment, the substrate 10 of the microfluidic device 1 is transparent for imaging. Hence, biological material can then be optically monitored in the spatially defined and separated cell channels 20. Alternatively, or in addition, a lid of the substrate 10, configured to be placed onto the substrate 10 or at least a portion thereof to enclose the spatially defined and separated cell channels 20, could be transparent for imaging if an optical monitoring is performed in step S2 and/or S5.

FIG. 8 is a scanning electron microscopy image showing part of the mold for a microfluidic device 1 shown in in $11 \times 10^3 \times$ magnification. The image indicates the cell channels 20 and the channel obstructions 25 close to the second ends 24 of the cell channels 20.

The channel obstruction 25 may be in the form of a restriction or obstruction restricting the dimension, such as width and/or height, of the spatially defined and separated cell channels 20. This restriction or obstruction will thereby prevent selected cells having size larger than the restricted width and/or height from passing the channel obstruction 25. However, smaller cells and biological and non-biological material having a size smaller than the restricted width and/or height can pass the channel obstruction and will thereby washed out into the flow output channel 40 and the third fluid port 41.

FIGS. 7 and 8 illustrate reference channels 50 that are cell channels lacking any channel obstruction. These reference channels 50 could be used as reference when taking images of the microfluidic device 1 to have a reference image level with only culture medium, such as the biological sample, without any cells that can be subtracted from the image data of the cell channels 20.

FIG. 8 also illustrates a dot barcode 60 imprinted into the substrate 10. The dot barcode 60 can be used to identify the spatially defined and separated cell channels 20 in the microfluidic device 1. Alternative individual channel identifies could be imprinted into the substrate 10 as shown in FIGS. 12-15 of [2].

In an embodiment relating to use of a microfluidic device 1 as described above, step S4 of FIG. 1 comprises loading the test agent into the second fluid port 33 allowing the test agent to flow through the flow input channel 30, the spatially defined and separated cell channels 20, the flow output channel 40 and out from the third fluid port 41 and optionally out from the first fluid port 31.

Figure 9:
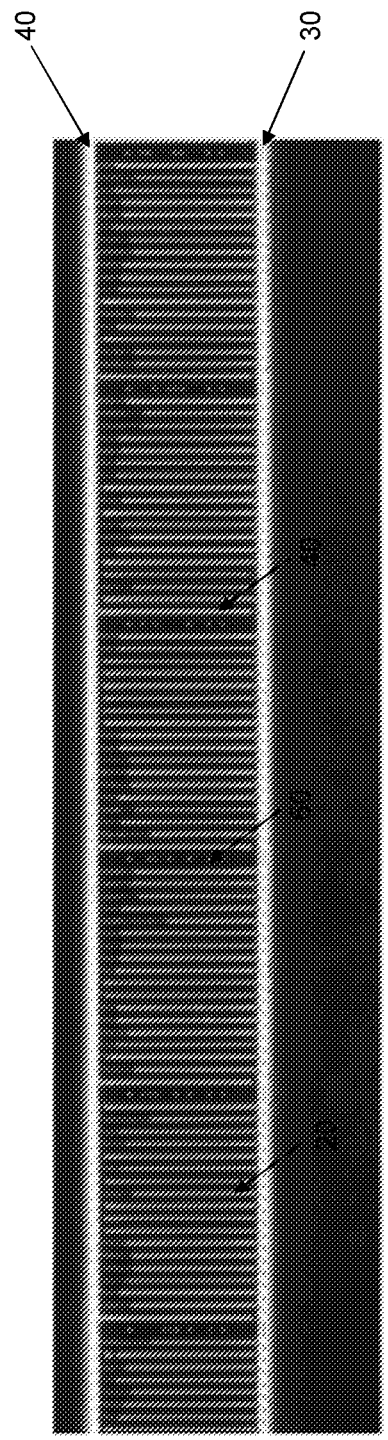
FIG. 9 is a phase contrast image of a part of a microfluidic device loaded with a biological sample.

FIG. 9 is a phase contrast image of a part of a microfluidic device loaded with a biological sample. In this image, cells present in the spatially defined and separated cell channels 20 correspond to the dark portion of the spatially defined and separated cell channels 20 facing the flow output channel 40, whereas the remaining light portions of the spatially defined and separated cell channels 20 comprise only the culture medium of the biological sample and no cells.

Figure 10:
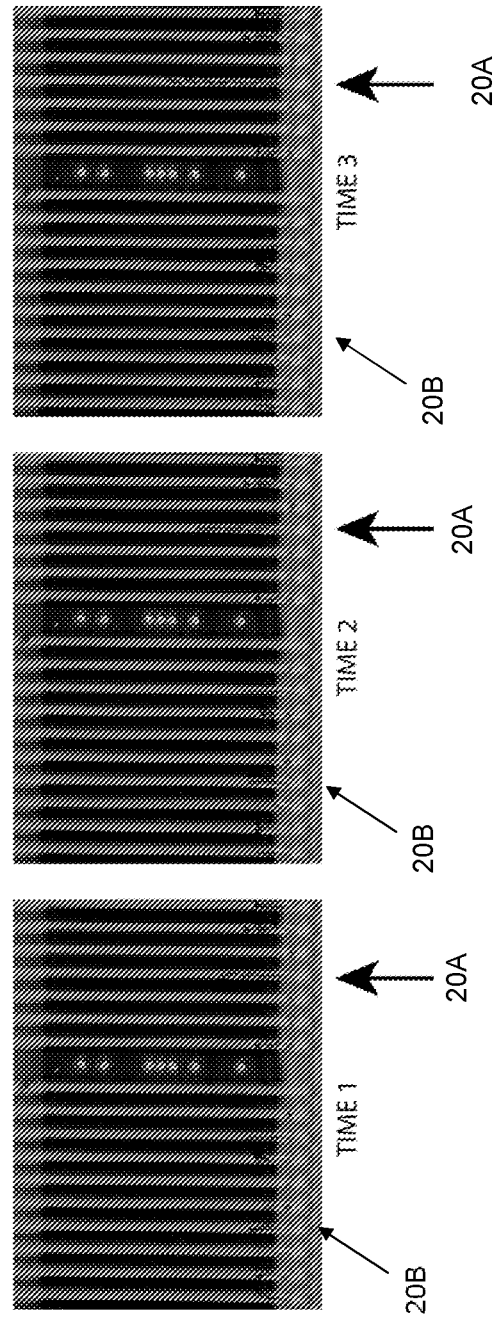
FIG. 10 are phase contrast images of a part of a microfluidic device at three different time instances following loading the microfluidic device with a biological sample.

FIG. 10 are phase contrast images of a part of a microfluidic device loaded with a biological sample taken at three different time instances. In these images, cells and non-cell material are indicated as longitudinal dark objects in the spatially defined and separated cell channels. Reference number 20A indicates a spatially defined and separated cell channel 20A that comprises cells that are growing. Hence, the number of cells present in that spatially defined and separated cell channel 20A increases when going from time 1 to time 2 and further to time 3. Reference number 20B indicates a spatially defined and separated cell channel 20B that comprises a cell not capable of growing in the particular culture medium or non-cell material. Thus, the number of cells or non-cell material in this spatially defined and separated cell channel 20B remains the same at all three time instances.

As is schematically illustrated by the three images in FIG. 10, only one of out of the shown spatially defined and separated cell channels 20A comprises cells that are viable and growing in the particular culture medium. All the remaining spatially defined and separated cell channels 20B comprise non-viable and non-growing cells or non-cell material.

FIG. 10 indicates that the vast majority of spatially defined and separated cell channels may contain biological material other than the target cells or non-biological material when loading a heterogeneous biological sample into a microfluidic device. Accordingly, there is need for a selection and identification of which spatially defined and separated cell channels to monitor in order to phenotype the target cells. Otherwise cells other than target cells and non-biological material would contaminate and thereby influence the phenotype determination of the target cells.

FIGS. 11A and 11B show length (FIG. 11A) and growth rate (FIG. 11B) as a function of time plotted for individual cell channels of a microfluidic device. These figures indicate that there is a large difference in phenotypic characteristics of cells in a heterogeneous biological sample and that a correct and reliable phenotyping would benefit from an initial identification and selection of spatially defined and separated cell channels according to the embodiments.

Figure 13:
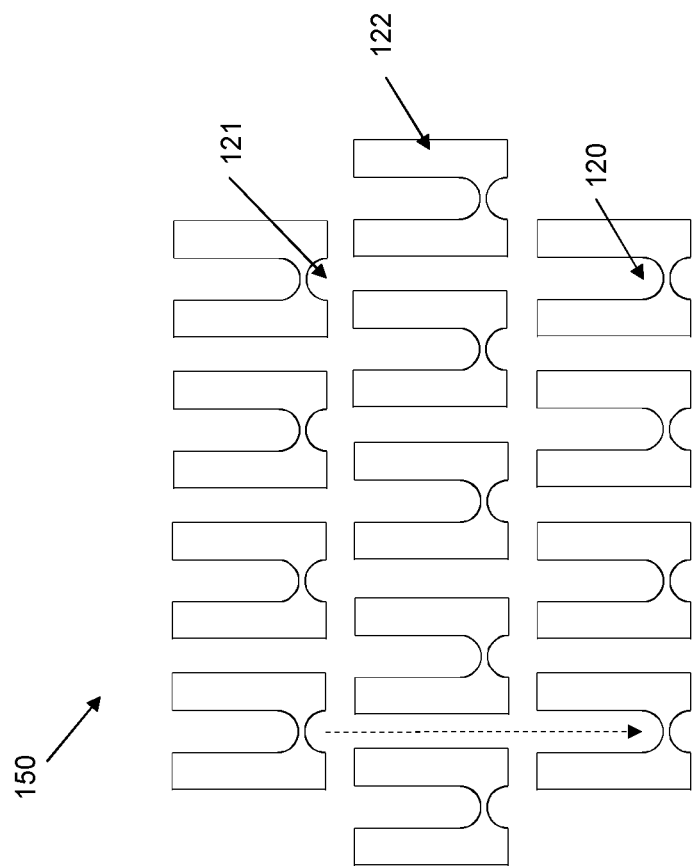
FIG. 13 is an illustration of the cell trap region in the microfluidic device of FIG. 12.
Figure 12:
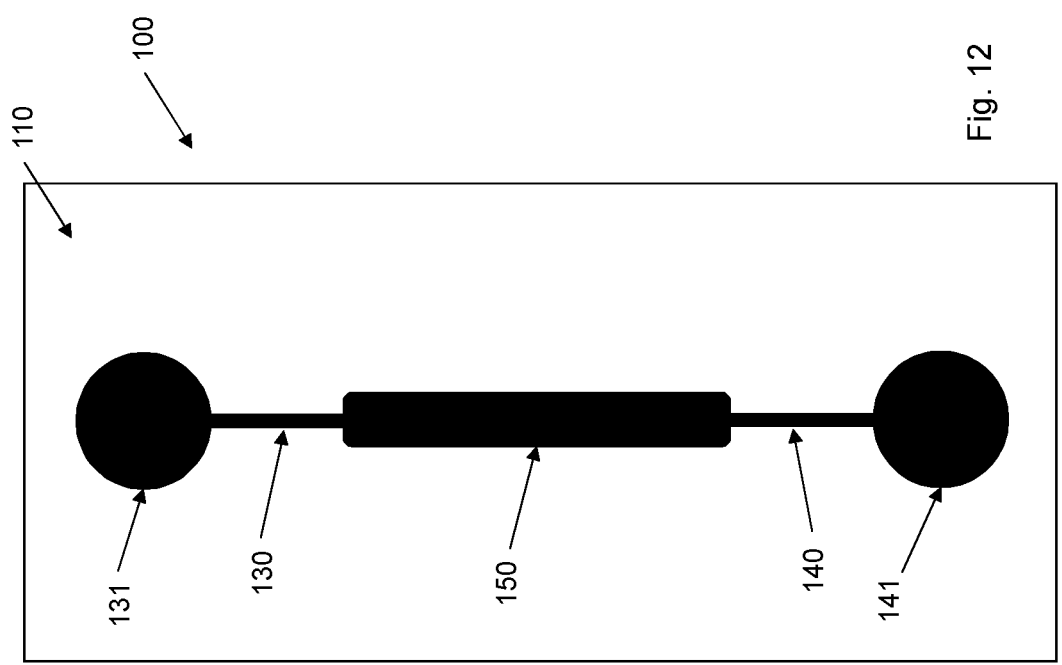
FIG. 12 is an illustration of a microfluidic device that can be used in the method for phenotyping according to another embodiment.

The embodiments are not limited to the particular microfluidic device described in the foregoing and illustrated in FIGS. 7 and 8. Also other microfluidic device comprising spatially defined and separated cell compartments could be used according to the embodiments. An example of such another microfluidic device is shown in FIGS. 12 and 13 and further in [4].

The microfluidic device 100 comprises a substrate 110, preferably transparent for imaging and, having a cell trap region 150 with spatially defined and separated cell traps 120 having a dimension, such as size and shape, to accommodate cells. The cell trap region 150 is in fluid connection with a first flow channel 130 having a first fluid port 131 and with a second flow channel 140 having a second fluid port 141.

A biological sample is loaded into the second fluid port 141 to allow the biological sample to flow through the second flow channel 140, into the cell trap region 150 and further into the first flow channel 130 and out from the first fluid port 131. Cells and non-cell material present in the biological sample will be captured in capture traps 121 forming the "backside" of so-called capture cups 122. When the flow is reversed, i.e., going from the first fluid port 131, into the first flow channel 130, the cell trap region 150, and further into the second flow channel 140 and out from the second fluid port 141 cells and non-cell material captured in the capture traps 121 will be transferred in the direction of the flow into the larger cell traps 120 of a co-aligned and downstream arranged capture cup 122 as schematically illustrated by the hatched arrow in FIG. 13.

In an embodiment, the capture caps 122 comprises a thin channel between a cell trap 120 in a capture cap 122 and a capture trap 121 in the capture cap 122. This thin channel then facilitates a flow of culture medium out through the cell trap 120 and further into the aligned capture trap 122. This optional thin channel of the capture cups 122 is, however, too small to allow any cells from passing through the thin channel.

The above described and illustrated microfluidic devices should merely be seen as illustrative examples of microfluidic devices that can be used in the method for phenotyping cells. Accordingly, other microfluidic devices having spatially defined and separated cell compartments can be used in the embodiments.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

REFERENCES

[1] Kim et al., Miniaturized Antimicrobial Susceptibility Test by Combining Concentration Gradient Generation and Rapid Cell Culturing, *Antibiotics*, 2015, 4(4): 455-466
[2] WO 2016/007068
[3] Baltekin et al., Fast Antibiotic Susceptibility Testing (FASTest) based on single cell growth rate measurements, bioRxiv preprint, 2016 (doi.org/10.1101/071407)
[4] Skelley et al., Microfluidic Control of cell Pairing and Fusion, *Nat Methods*, 2009, 6(2): 147-152
[5] Baltekin et al., Antibiotic susceptibility testing in less than 30 min using direct single-cell imaging, *PNAS*, 2017, 114(34): 9170-9175

The invention claimed is:

1. A method for determining a phenotypic response of cells, said method comprising:
   a) loading a biological sample comprising biological material including (i) target cells, and (ii) non-target contaminating cells and/or non-cell material into a microfluidic device comprising spatially defined and separated cell compartments to capture biological material in said spatially defined and separated cell compartments;
   b) monitoring biological material in said spatially defined and separated cell compartments for at least one target phenotype characteristic prior to exposing biological material in said spatially defined and separated cell compartments to a test agent;
   c) identifying a subset of said spatially defined and separated cell compartments as comprising target cells exhibiting said at least one target phenotype characteristic as determined based on said monitoring of biological material in said spatially defined and separated cell compartments in b), and
   identifying remaining spatially defined and separated cell compartments as comprising said non-target contaminating cells and/or said non-cell material not exhibiting said at least one target phenotype characteristic as determined based on said monitoring of biological material in said spatially defined and separated cell compartments in b);
   d) exposing biological material in said spatially defined and separated cell compartments to a test agent;
   e) monitoring target cells in said identified subset of said spatially defined and separated cell compartments; and
   f) determining a phenotypic response of said target cells to said test agent based on said monitoring of target cells in said identified subset of said spatially defined and separated cell compartments in e) while disregarding any phenotypic response of said non-target contaminating cells and/or said non-cell material in said remaining spatially defined and separated cell compartments.

2. The method according to claim 1, wherein after step a), the method further comprises:

exposing said biological material in said spatially defined and separated cell compartments to a culture medium, wherein step b) comprises monitoring biological material exposed to said culture medium in said spatially defined and separated cell compartments for said at least one target phenotype characteristic.

3. The method according to claim 2, wherein said test agent is provided in a culture medium.

4. The method according to claim 1, wherein identifying said subset of said spatially defined and separated cell compartments comprises:

identifying target cells exhibiting said at least one target phenotype characteristic as determined based on said monitoring of biological material in said spatially defined and separated cell compartments in b); and selecting said subset of said spatially defined and separated cell compartments as a subset of said spatially defined and separated cell compartments comprising said identified target cells.

5. The method according to claim 1, wherein monitoring biological material comprises monitoring, at multiple time instances, biological material in said spatially defined and separated cell compartments.

6. The method according to claim 1, wherein monitoring target cells comprises monitoring, at multiple time instances, target cells in said identified subset of said spatially defined and separated cell compartments.

7. The method according to claim 1 wherein monitoring biological material comprises taking at least one image of said spatially defined and separated cell compartments.

8. The method according to claim 7, wherein identifying said subset of said spatially defined and separated cell compartments comprises:

processing said at least one image for detection of said spatially defined and separated cell compartments and biological material in said spatially defined and separated cell compartments;

determining at least one respective phenotype characteristic of biological material in said spatially defined and separated cell compartments based on said processing;

identifying target cells as biological material in said spatially defined and separated cell compartments and having at least one respective determined phenotype characteristic corresponding to said at least one target phenotype characteristic; and selecting said subset of said spatially defined and separated cell compartments as a subset of said spatially defined and separated cell compartments comprising said identified target cells.

9. The method according to claim 1, wherein loading said biological sample comprises loading a biological sample comprising biological material including (i) said target cells, and (ii) said non-target contaminating cells and/or said non-cell material into said microfluidic device to capture biological material in said spatially defined and separated cell compartments;

identifying said subset of said spatially defined and separated cell compartments comprises:

identifying a subset of said spatially defined and separated cell compartments as comprising target cells exhibiting said at least one target phenotype characteristic as determined based on said monitoring of biological material in said spatially defined and separated cell compartments in b); and identifying remaining spatially defined and separated cell compartments as comprising non-target contaminating cells and/or non-cell material not exhibiting said at least one target phenotype characteristic as determined based on said monitoring of biological material in said spatially defined and separated cell compartments in b); and monitoring target cells comprises:

taking at least one image of said spatially defined and separated cell compartments; and processing said at least one image for detection of said identified subset of said spatially defined and separated cell compartments and target cells in said identified subset of said spatially defined and separated cell compartments while disregarding said remaining spatially defined and separated cell compartments and non-target contaminating cells and/or said non-cell material in said remaining spatially defined and separated cell compartments.

10. The method according to claim 1, wherein said target phenotype characteristic is selected from a group consisting of growth rate, shape, size, form of growth rate curve defining growth rate over time, form of length curve defining length of a portion of a spatially defined and separated cell compartment occupied by cells or non-cell material over time, form of area curve defining area of a spatially defined and separated cell compartment occupied by cells or non-cell material over time, color, optical density, electrical conductivity, heat production, surface antigen composition, absorption spectra, and a mixture thereof.

11. The method according to claim 1, wherein after step a), the method further comprises:

adding a labeled probe to said spatially defined and separated cell compartments, wherein step b) comprises monitoring said labeled probe in said spatially defined and separated cell compartments; and step c) comprises identifying said subset of said spatially defined and separated cell compartments as comprising target cells exhibiting at least one target phenotype characteristic as determined based on said monitoring of said labeled probe in said spatially defined and separated cell compartments.

12. The method according to claim 1, wherein said test agent is an antibiotic; and step f) comprises determining a susceptibility of said target cells to said antibiotic based on said monitoring of target cells in said identified subset of said spatially defined and separated cell compartments.

13. The method according to claim 1, wherein said test agent is a cytostatic; and step f) comprises determining a susceptibility of said target cells to said cytostatic based on said monitoring of target cells in said identified subset of said spatially defined and separated cell compartments.

14. The method according to claim 1, wherein step e) comprises:

taking at least one image of said spatially defined and separated cell compartments; and processing said at least one image for detection of said identified subset of said spatially defined and separated cell compartments and target cells in said identified subset of said spatially defined and separated cell compartments while disregarding said remaining spatially defined and separated cell compartments and non-target contaminating cells and/or non-cell material in said remaining spatially defined and separated cell compartments.

15. The method according to claim 1, wherein said target phenotype characteristic is selected from a group consisting of growth rate, shape, form of growth rate curve defining growth rate over time, form of length curve defining length of a portion of a spatially defined and separated cell compartment occupied by cells or non-cell material over time, form of area curve defining area of a spatially defined and separated cell compartment occupied by cells or non-cell material over time, color, optical density, electrical conductivity, heat production, surface antigen composition, absorption spectra, and a mixture thereof.

* * * * *